United States Patent
Yamaguchi et al.

(10) Patent No.: US 6,397,656 B1
(45) Date of Patent: Jun. 4, 2002

(54) SYSTEM AND METHOD FOR DETECTING LIQUID SERVING AS OBJECT TO BE DETECTED IN VESSEL USING ULTRASONIC SENSOR

(75) Inventors: Hirotaro Yamaguchi; Osamu Suzuki, both of Shibuya-Ku; Yukio Katagishi, Mitaka; Huaigang Zang, Mitaka; Tetsuo Takahashi, Mitaka; Hidetaka Kizaki, Mitaka; Masao Iwamoto, Mitaka, all of (JP)

(73) Assignees: Yamatake Corporation; Kasuga Denki Kabushiki Kaisha, both of Tokyo-To (JP)

( * ) Notice: Subject to any disclaimer, the term of this patent is extended or adjusted under 35 U.S.C. 154(b) by 0 days.

(21) Appl. No.: 09/489,853

(22) Filed: Jan. 24, 2000

(30) Foreign Application Priority Data

Jan. 25, 1999 (JP) ............................................. 11-015899
Sep. 14, 1999 (JP) ............................................. 11-261084

(51) Int. Cl.$^7$ ............................ G01N 29/00; G01V 13/00
(52) U.S. Cl. .................... 73/1.82; 73/290 V; 73/602
(58) Field of Search .................... 73/1.82, 1.83, 73/1.86, 1.73, 290 V, 602

(56) References Cited

U.S. PATENT DOCUMENTS

| 4,299,114 A | * | 11/1981 | Silvermetz et al. ....... 73/290 V |
| 4,811,595 A | * | 3/1989 | Marciniak et al. ........ 73/290 V |
| 5,511,041 A | * | 4/1996 | Michalski .................... 367/99 |
| 5,635,619 A | * | 6/1997 | Udpa et al. ................... 73/1.82 |
| 5,755,136 A | * | 5/1998 | Getman et al. ........... 73/290 V |
| 5,777,860 A | * | 7/1998 | Halbert ........................ 363/34 |
| 5,836,192 A | * | 11/1998 | Getman et al. ........... 73/290 V |
| 5,883,309 A | * | 3/1999 | Vossiek et al. ............... 73/602 |
| 5,991,234 A | * | 11/1999 | Sejalon et al. ............... 367/13 |

* cited by examiner

*Primary Examiner*—Hezron Williams
*Assistant Examiner*—Rose M. Miller
(74) *Attorney, Agent, or Firm*—Stevens, Davis, Miller & Mosher, LLP

(57) ABSTRACT

An operating frequency setting unit outputs an ultrasonic emitting command to a variable oscillator circuit in an operating frequency setting mode to cause a detector to emit an ultrasonic wave a plurality of times while varying the frequency thereof. At this time, emission or reflected waveform data are inputted via a band pass filter to detect a resonance frequency of a system including the piezoelectric element of the detector and an LPG tank on the basis of the difference between attenuation characteristics of waveforms. The detected resonance frequency is registered in a memory part as an operating frequency. Thus, it is possible to provide a general purpose ultrasonic sensor usable for any one of a plurality of vessels having any wall thickness and material when an object is detected while the detector is mounted on the outside face of a vessel.

12 Claims, 12 Drawing Sheets

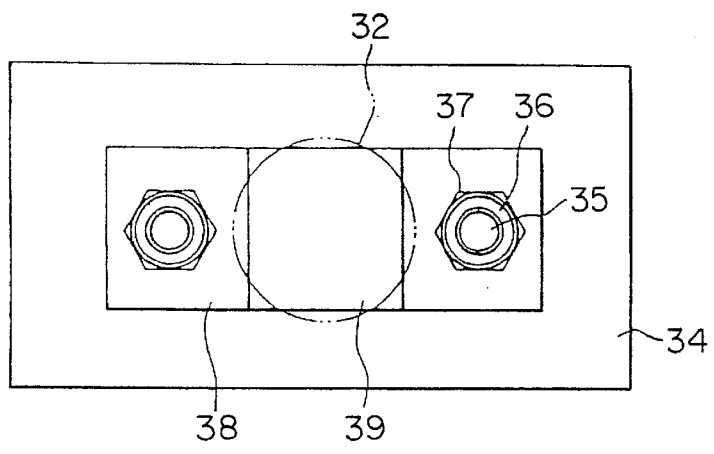
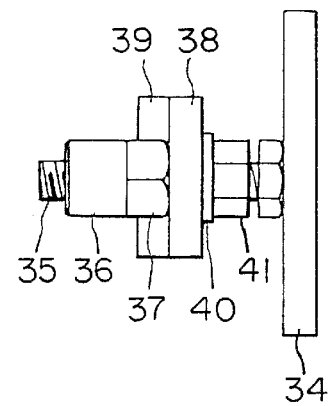
F I G. 9A    F I G. 9C
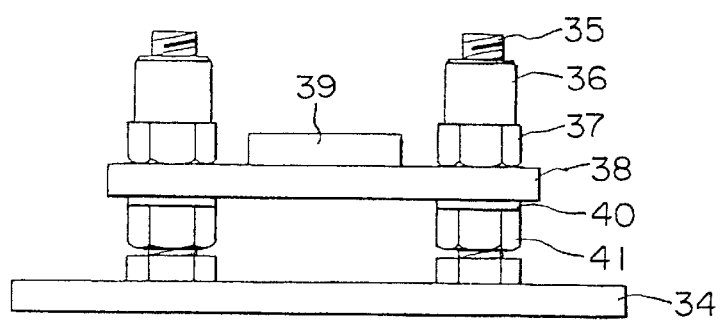
F I G. 9B

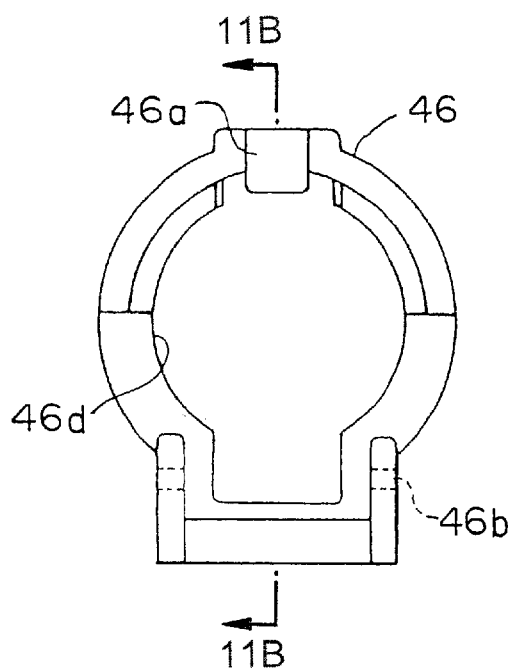
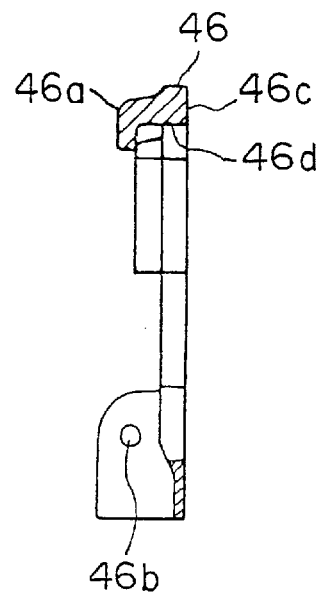
F I G. 11A  F I G. 11B
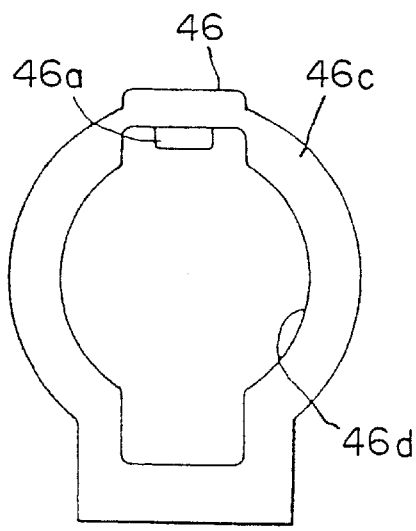
F I G. 11C

SYSTEM AND METHOD FOR DETECTING LIQUID SERVING AS OBJECT TO BE DETECTED IN VESSEL USING ULTRASONIC SENSOR

BACKGROUND OF THE INVENTION

The present invention relates generally to a system and method for detecting the liquid level and storage amount of a liquid stored in a vessel using an ultrasonic sensor by providing a detector outside a pressurized vessel to emit ultrasonic waves from the outside of the vessel to the inside thereof.

A typical ultrasonic sensor is designed to emit an ultrasonic pulse toward an object to be detected (the surface of a liquid) to receive a reflected wave, which is reflected on the object, to measure a period of time from the ultrasonic pulse emitting time to the reflected wave receiving time to detect the object (the liquid level of the liquid). Therefore, a material for inhibiting the smooth propagation of ultrasonic waves is not preferably provided between a detector for transmitting/receiving the ultrasonic pulse and the object to be detected. Thus, there is proposed a liquid measuring system wherein piezoelectric active means of a piezoelectric element for emitting a sound wave is provided on the bottom of a vessel, such as a fuel tank of an automotive vehicle and wherein when the sound wave emitted from the bottom of the vessel is reflected on the liquid level to reach the bottom again, the sound wave is received to measure a period of time from the emission time to the receiving time to detect the distance between the bottom and the liquid level (e.g., see International Publication No. WO98/04889).

However, when a liquid serving as an object to be detected, such as liquefied petroleum gas (LPG) or gasoline, is stored in a pressurized pressure vessel, so that it is difficult to provide a detector in the vessel, the detector is unavoidably provided outside of the vessel to transmit/receive the ultrasonic pulse between the detector and the object via the thick wall portion of the vessel. In particular, the main current of, e.g., a level sensor for detecting a liquid level in an LPG tank, uses mechanical means. If an ultrasonic sensor is used as the level sensor, a detector is mounted on the outside bottom face of the tank since the LPG tank is a pressure vessel and since it is difficult to provide the detector in the vessel.

In such a construction, the ultrasonic wave emitted from the detector passes through the thick bottom wall portion of the tank to reach the liquid level via the liquid to be reflected on the liquid level to pass through the thick bottom wall portion of the tank via the liquid again to be received by the detector. Therefore, in order to precisely detect the liquid level, the transmittance of the ultrasonic wave in the thick wall portion of the bottom plate of the tank (pressure vessel) must be high.

However, in order to enhance the transmittance of the ultrasonic wave in the thick wall portion of the bottom plate of the tank, the oscillation frequency of the ultrasonic wave emitted from the detector must be optimally set in accordance with the wall thickness and material of the tank. That is, with respect to the relationship between the transmittance and the wall thickness of the tank, it is known that the transmittance is good when the wall thickness is integer times as large as $(1/2)\lambda$ or $(1/4)\lambda$ assuming that the wavelength of an ultrasonic wave is $\lambda$. Therefore, assuming that the wall thickness is t, the oscillation frequency is f, the sound speed is c, and an integer is n, then $\lambda = c/f$, so that the wall thickness t is expressed by the following formula (1) or (2).

Furthermore, whether the wall thickness t is expressed by the formula (1) or (2) is determined by whether the piezoelectric element has a vibrating plane(s) on one side or both sides.

$$t = n \cdot (\lambda/2) = n \cdot c/2f \qquad (1)$$

$$t = n \cdot (\lambda/4) = n \cdot c/4f \qquad (2)$$

With respect to the relationship between the transmittance and the material of the tank, it is known that the transmittance is good when the value of the resonance frequency, which is a characteristic value peculiar to the material, is close to the value of the operating frequency of the piezoelectric element of the detector. Thus, conventionally, when the detector is mounted on the outside bottom face of the LPG tank, ultrasonic sensor manufacturers previously examine the wall thickness and material of the tank to select sensors having the optimum operating frequency from existing standard products, or new product ultrasonic sensors if there are no sensors having the optimum operating frequency in the existing standard products.

However, the wall thickness and material of the tank vary in accordance with working environment or other conditions, so that there are some cases where an operating frequency having been applied to a certain tank can not be applied to another tank.

In such cases, the sensor manufacturers must select sensors having a desired operating frequency from the existing standard products again, or new product ultrasonic sensors if there are no sensors having the desired operating frequency in the existing standard products. That is, conventional ultrasonic sensors are exclusive goods having an operating frequency according to a specific working environment, and do not have flexibility, so that the sensors can not be used if the wall thickness or material of a vessel is changed. An example of such a conventional ultrasonic sensor is proposed in GB patent No. 2284053A.

SUMMARY OF THE INVENTION

It is therefore an object of the present invention to eliminate the aforementioned problems and to provide a detection system having a general ultrasonic sensor applicable if the thickness and/or material of a vessel for storing therein a liquid serving as an object to be detected is changed, and an object detecting method using the above described ultrasonic sensor.

In order to accomplish the aforementioned and other objects, according to a first aspect of the present invention, an object detecting system using an ultrasonic sensor, comprises: a detector mounted on an outside face of a vessel; and a detection operation control circuit for causing the detector to emit an ultrasonic wave toward an object to be detected in the vessel and to receive a reflected wave from the object, and for controlling an object detecting operation an the basis of a measured period of time between the ultrasonic wave emitting time and the reflected wave receiving time, wherein the detection operation control circuit has operating frequency setting means for causing the detector to emit the ultrasonic wave a plurality of times while previously varying a frequency before the object detecting operation is carried out, for inputting an emission waveform or a reflected waveform at that time, for detecting a resonance frequency of the system comprising the detector and the vessel on the basis of an analysis of the inputted waveform, and for setting the detected resonance frequency as an operating frequency.

In the object detecting system according to the first aspect of the present invention, the detector may emit the ultrasonic wave in response to of the input of a rectangular pulse signal. In addition, the operating frequency setting means may input the emission waveform or reflected waveform, which is used for the analysis, via a band pass filter so as to prevent a false detection of the resonance frequency due to a high harmonic oscillation. Moreover, the vessel may be used for storing therein a liquid, and the operating frequency setting means may determine whether the analysis is carried out using the emission waveform or the reflected waveform, on the basis of the presence of the liquid in the vessel.

Moreover, the analysis of the emission waveform or reflected waveform carried out by the operating frequency setting means may include the selection of a waveform having the minimum attenuated degree of an attenuation waveform from the emission waveform and the reflected waveform, and the derivation of an operating frequency of the selected waveform. In addition, the analysis of the emission waveform or reflected waveform carried out by the operating frequency setting means may include the selection of a waveform having the minimum impedance including the detector and the vessel, and the derivation of an operating frequency of the selected waveform. In addition, the operating frequency setting means may shift each input timing from the last input timing by a predetermined period of time when a plurality of emission waveforms or reflected waveforms are inputted on the basis of the plurality of emissions of the ultrasonic wave. Moreover, the detector may have a piezoelectric element formed of a low Q material having a gentle resonance waveform (Q) so that an acutance of the resonance waveform decreases.

In order to accomplish the aforementioned and other objects, according to a second aspect of the present invention, there is provided an object detecting method using an ultrasonic sensor having a detector on an outside face of a vessel for causing the detector to emit an ultrasonic wave toward an object to be detected in the vessel and to receive a reflected wave from the object and for detecting the object on the basis of a measured period of time between the ultrasonic wave emitting time and the reflected wave receiving time, the object detecting method comprising the steps of: causing the detector to emit an ultrasonic wave a plurality of times while previously varying a frequency before the object is detected; inputting an emission waveform or a reflected waveform at that time; detecting a resonance frequency of the system comprising the detector and the vessel on the basis of an analysis of the inputted emission or reflected waveform; setting the detected resonance frequency as an operating frequency; and causing the detector to emit an ultrasonic wave toward the object to be detected in the vessel, on the basis of the set operating frequency.

As described above, according to the present invention, when an object is detected while a detector is mounted on the outside face of a vessel, the detector emit an ultrasonic wave a plurality of times while previously varying the frequency thereof. At this time, an emission or reflected waveform is inputted to detect a resonance frequency of the system comprising the detector and the vessel on the basis of the analysis of the inputted waveform to set the detected resonance frequency as an operating frequency. Therefore, it is possible to provide a general ultrasonic sensor, which can be used for any vessels having any wall thickness and material and which can be installed by only a user without the need of the cooperation with the sensor manufacturer.

BRIEF DESCRIPTION OF THE DRAWINGS

In the drawings:

FIG. 9A is a plan view of detector case pressing means, FIG. 9B is a front view thereof, and FIG. 9C is a side view thereof;

FIG. 11A is a plan view of a mounting base of FIG. 10, FIG. 11B is a sectional view thereof, and FIG. 11C is a bottom view thereof;

DESCRIPTION OF THE PREFERRED EMBODIMENTS

Figure 1:
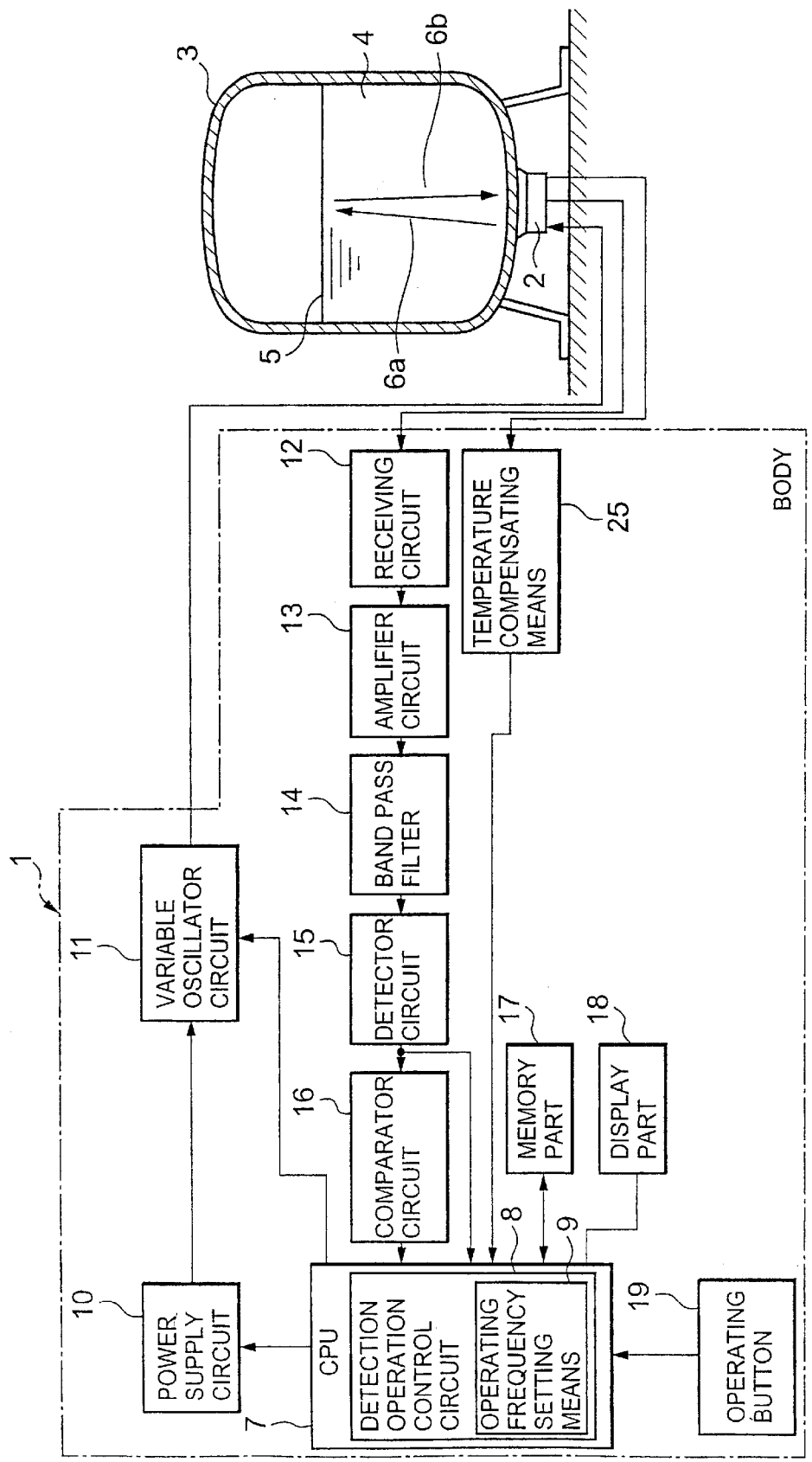
FIG. 1 is a block diagram of the first preferred embodiment of an object detecting system using an ultrasonic sensor according to the present invention.

Referring now to the accompanying drawings, the preferred embodiments of the present invention will be described below. FIG. 1 is a block diagram of the first preferred embodiment of an ultrasonic sensor according to the present invention. The ultrasonic sensor comprises a body 1 and a detector 2. The ultrasonic sensor is mounted on the outside bottom face of an LPG tank 3 of a predetermined material (e.g., stainless steel) having a predetermined wall thickness. A liquid 4 (LP gas) is stored in the LPG tank 3. An ultrasonic wave 6a emitted from the detector 2 is reflected on a liquid level 5, and a reflected wave 6b is received by the detector 2. In the first preferred embodiment, a piezoelectric element (not shown) of the detector 2 uses a so-called "low Q material" having a relatively gentle acutance near a resonance point on a resonance characteristic curve. As the low Q material, there is lead zirconate titanate (PZT) produced as the low Q material.

The body 1 has a CPU 7 which includes a detection operation control circuit 8 having operating frequency setting means 9. The body 1 also has a variable oscillator circuit 11 for outputting an oscillation pulse to the piezoelectric element of the detector 2 on the basis of a electric power supply from a power supply circuit 10, a receiving circuit 12 for inputting a signal indicative of the reflected wave 6b or a signal indicative of the emitted ultrasonic wave 6a from the detector 2, an amplifier circuit 13 for amplifying the signal inputted by the receiving circuit 12, a band pass filter 14 for filtering a signal from the amplifier circuit 13, a detector circuit 15 for detecting a signal from the band pass filter 14, a comparator circuit 16 for comparing a signal from the detector circuit 15 with a preset threshold to determine whether this signal is a noise, a memory part 17 (of, e.g., an electrically erasable and programmable read only memory (EEPROM)) for storing the value of an operating frequency set by the operating frequency setting means 9, a display part 18 capable of displaying the value of the set operating frequency, and an operating button 19 for compulsorily resetting the set operating frequency. The detector 2 also has temperature detecting means (not shown), such as a thermistor, for detecting the temperature of the outside face of the tank 3. A temperature signal detected by the temperature detecting means is supplied to temperature compensating means 25 to be supplied to the CPU 7 as a temperature correction signal.

Figure 2:
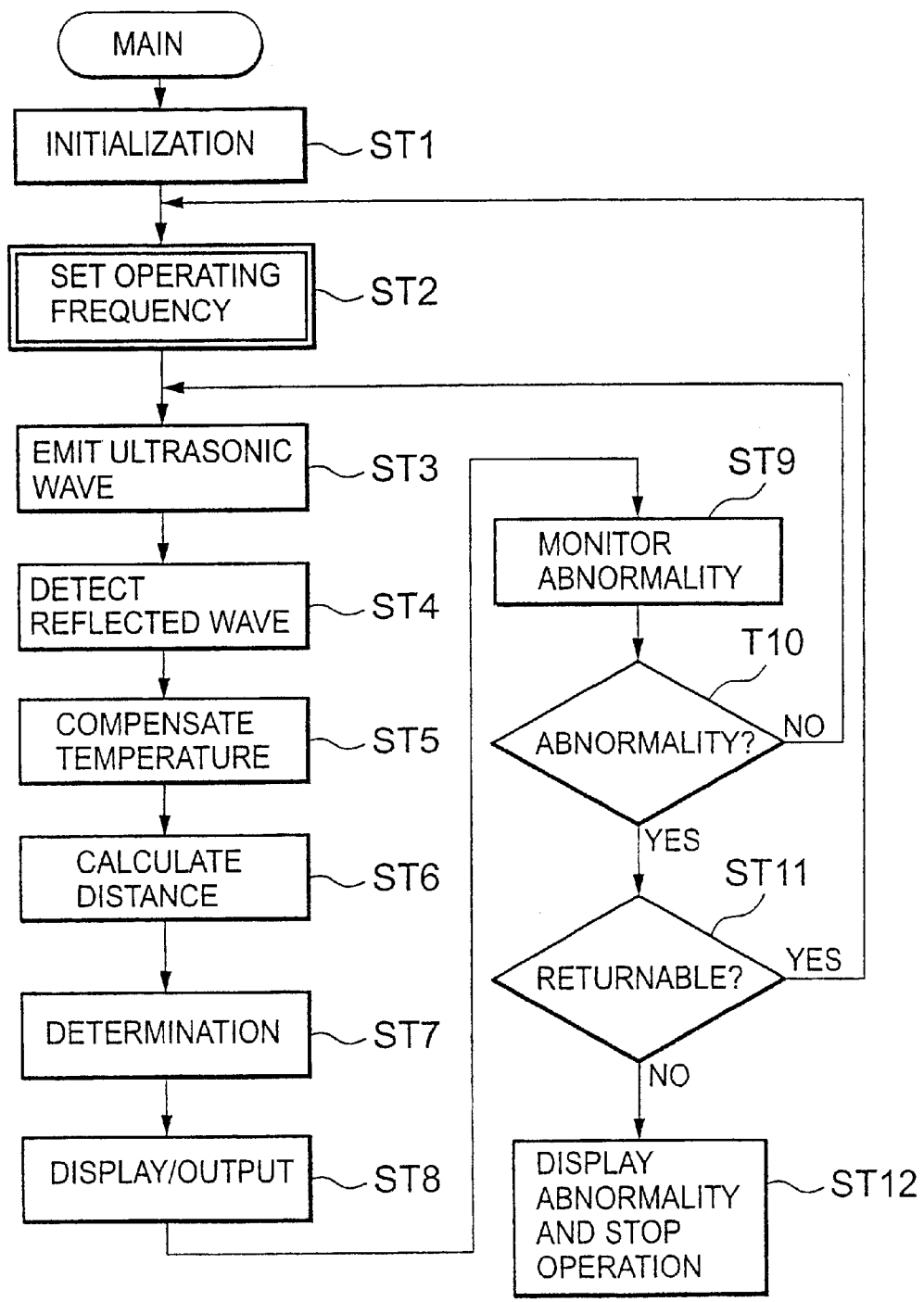
FIG. 2 is a flow chart for explaining the operation of the detecting system of FIG. 1.
Figure 3:
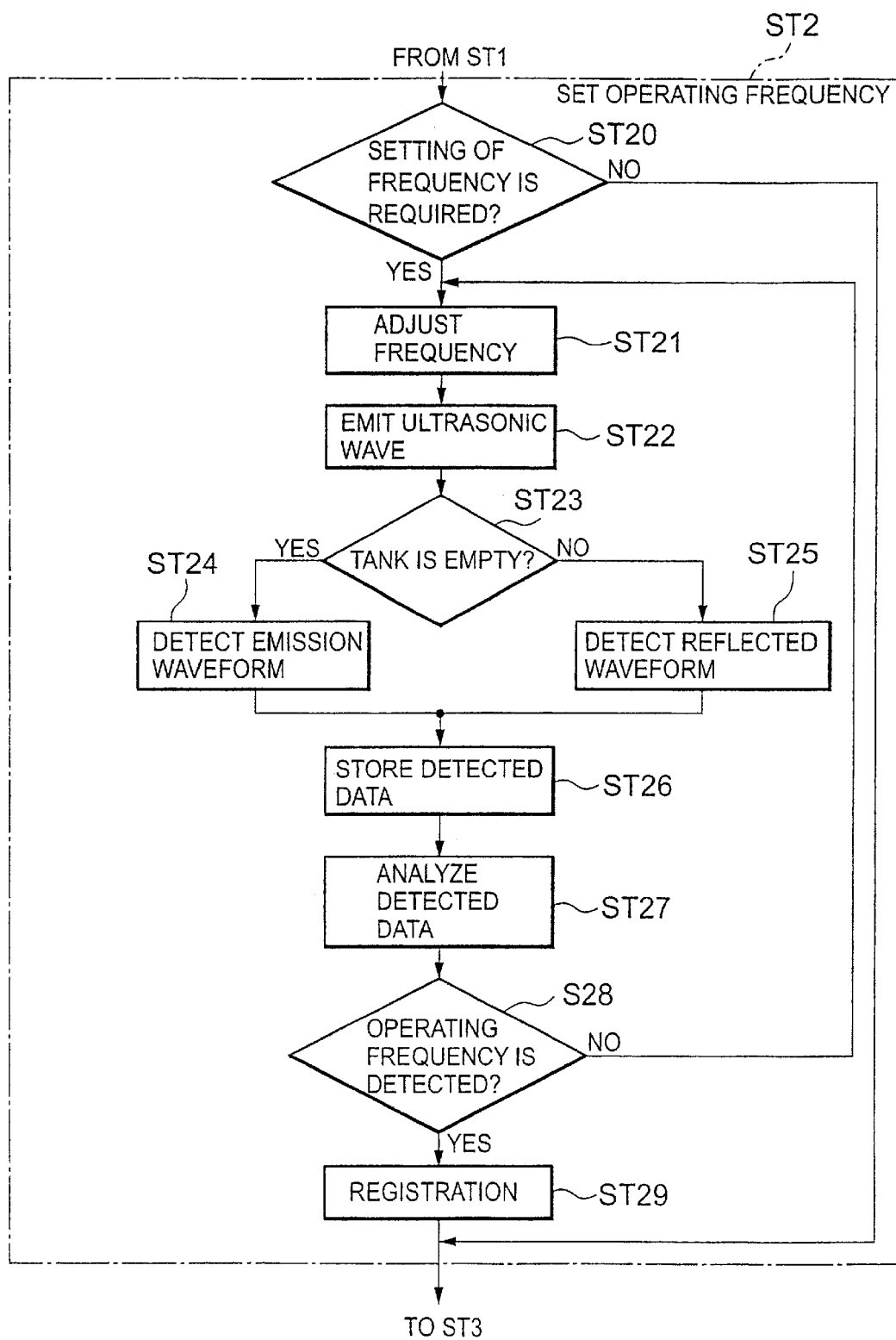
FIG. 3 is a flow chart showing the detailed operation in an operating frequency setting mode at step ST2 of the flow chart of FIG. 2.

Referring to the flow charts of FIGS. 2 and 3, the operation of the first preferred embodiment with the above described construction will be described below. In FIG. 2, after the detection operation control circuit 8 of the CPU 7 performs initialization (step ST1), and the detection operation control circuit 8 is in an operating frequency setting mode to set an operating frequency by the function of the operating frequency setting means 9 (step ST2). The detailed contents of step ST2 will be described later referring to FIG. 3.

After the operating frequency is set at step ST2, the detection operation control circuit 8 outputs a detection starting command to the variable oscillator circuit 11 (step ST3). Thus, the variable oscillator circuit 11 outputs a rectangular oscillation pulse having a frequency set at step ST2 to the detector 2.

The detector 2 emits an ultrasonic wave 6a into the LPG tank 3 in response to the input of the oscillation pulse, and receives a reflected wave of the ultrasonic wave from the liquid level 5 to output the reflected wave 6b to the receiving circuit 12. The reflected wave 6b inputted to the receiving circuit 12 is transmitted to the CPU 7 via the amplifier circuit 13, the detector circuit 14, the band pass filter 15 and the comparator circuit 16. Then, the detection operation control circuit 8 detects the reflected wave (step ST4).

Then, the detection operation control circuit 8 performs a temperature compensating processing (step ST5). This is a processing for varying the value of a coefficient, which is used for calculating the distance between the detector 2 and the liquid 5, in accordance with the temperature of the liquid 4, since the propagation speed of the ultrasonic wave 6 varies in accordance with the temperature of the liquid 4. Since it is difficult to directly detect the temperature of the liquid in the tank 3, the temperature of the outside face of the tank 3 is detected by the thermistor or the like, and the detected temperature is converted into a temperature compensated signal by the temperature compensating means 25 to be used. After the temperature compensating processing is performed, the detection operation control circuit 8 calculates the distance between the detector 2 and the liquid level 5 (step ST6), and determines whether the position of the detected liquid level 5 has not been calculated by false detection due to noises or whether it is an obstacle other than the liquid level (step ST7). Then, after the detection operation control circuit 8 determines that the calculated liquid level 5 is normal, the value of the distance is displayed on the display part 18, and a distance signal indicative thereof is outputted to a control device (not shown) (e.g., an LP gas residual quantity monitoring device) (step ST8).

In this way, the liquid level of the liquid 4 in the LPG tank 3 is detected by means of the ultrasonic sensor. In this preferred embodiment, also during operation, it is always monitored whether the operating frequency is not abnormal (steps ST9 through ST12). For example, the mounting state of the detector 2 mounted on the bottom of the LPG tank 3 is slacked during operation, there are some cases where the operating frequency set at step ST2 is no longer valid since the resonance frequency of the system comprising the piezoelectric element of the detector 2 and the LPG tank 3 varies. In such cases, since the voltage of the piezoelectric element of the detector 2 varies, the operating frequency setting means 9 monitors abnormality on the basis of the detection of the variation in voltage of the piezoelectric element (step ST9). Then, the value of the detected voltage is compared with a predetermined threshold to determine abnormality (step ST10). when there is no abnormality, the routine returns to step ST3 to continue operation, and when there is abnormality, it is determined whether the degree of the abnormality is a degree capable of being returned to the original normal state by resetting the operating frequency (step ST11). when it is determined that the degree of the abnormality is the degree capable of being returned, the abnormality is displayed on the display part 18, and operation is stopped (step ST12).

Referring to the flow chart of FIG. 3, the detailed contents of the operating frequency setting mode at step ST2 of FIG. 2 will be described below. First, the operating frequency setting means 9 determines whether it is required to set an operating frequency (step ST20). In this case, since the operating frequency has not been yet set immediately after the ultrasonic sensor is provided, it is naturally determined that "it is required", and after once the operating frequency is set, it is usually determined that "it is not required". However, when YES is determined at step ST11, i.e., when the operating frequency is abnormal and when the degree of the abnormality is the degree capable of being returned to the original state, it is determined that "it is required" even after the operating frequency is set.

After it is determined at step ST20 that it is required to set the frequency, the operating frequency setting means 9 adjusts the frequency (step ST21), and emits an ultrasonic wave (step ST22). However, it is assumed that when the first ultrasonic wave is emitted, the value of the frequency is not varied in the adjustment of the frequency at step ST21, and the ultrasonic wave is emitted at a frequency set when being shipped from a sensor manufacturer. Then, the operating frequency setting means 9 determines whether the LPG tank 3 is empty, i.e., whether the liquid level 5 in the LPG tank 3 has been detected, on the basis of the emission of the ultrasonic wave (step ST23). Furthermore, there are considered various techniques for varying an oscillation frequency in the variable oscillator circuit 11. As an example, there is considered a technique for variably controlling the gate voltage of the field effect transistor (FET) in the variable oscillator circuit 11. By this technique, it is possible to vary the oscillation frequency since the "R", i.e., the resistance component, in a CR oscillator circuit is varied.

When it is determined that the LPG tank is empty, the ultrasonic waveform 6a emitted from the detector 2 is detected since there is no reflected waveform (step ST24). On the other hand, when it is determined that the LPG tank is not empty, i.e., when the liquid 4 is supplied into the LPG tank 3, the reflected waveform 6b from the detector 2 is detected (step ST25).

The operating frequency setting means 9 stores waveform data, which are detected at step ST24 or ST25, in its memory part (not shown) as the last data (step ST26), and analyzes the current data using the stored last data (step ST27). Referring to the waveform illustrations of FIGS. 4A and 4B, the contents of analysis in this case will be described below.

Figure 4A:
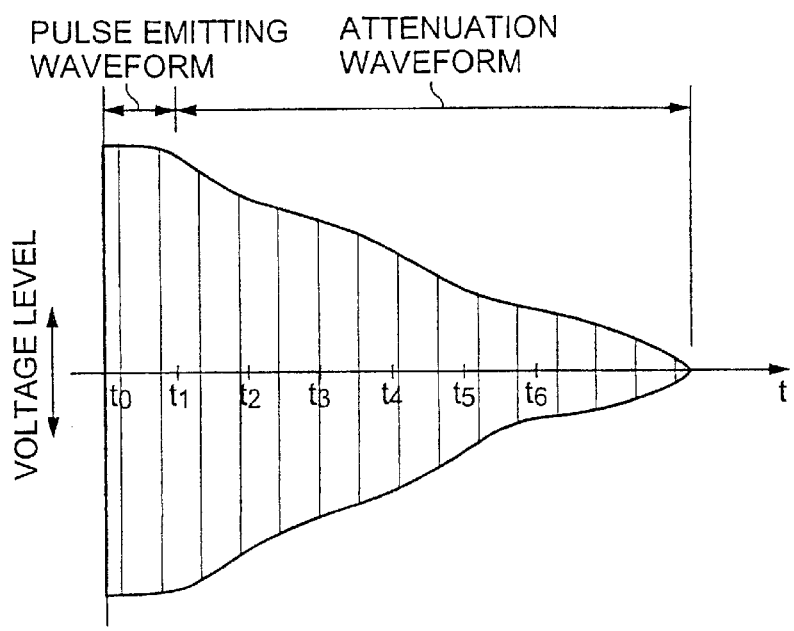
FIGS. 4A and 4B are waveform illustrations showing emission waveforms of a detector 2 of FIG. 1 during resonance and non-resonance.
Figure 4B:
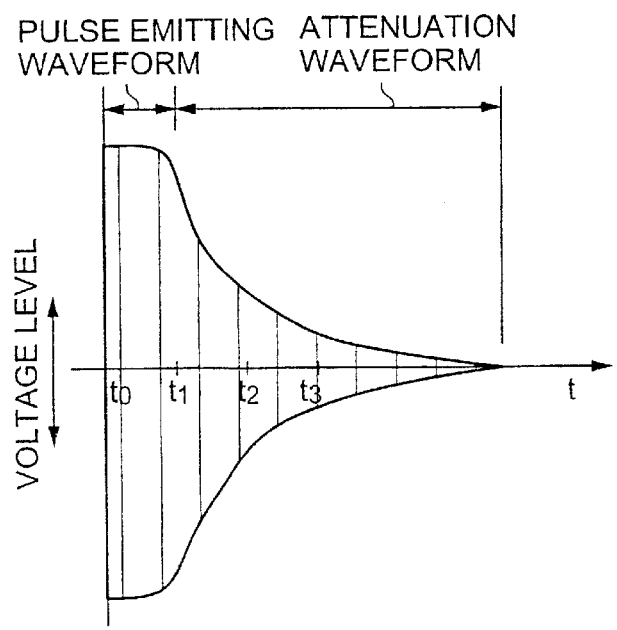

FIGS. 4A and 4B show the emission waveform 6a of the detector 2 during resonance and non-resonance. As shown in these figures, the emission waveform comprises the pulse emitting waveform 6a while an oscillation pulse is outputted from the variable oscillator circuit 11 to the detector 2, and an attenuation waveform thereafter. For example, assuming that the variable oscillator circuit 11 outputs an oscillation pulse to the piezoelectric element of the detector 2 in a period of time between time t0 and time t1, although the piezoelectric element continues to vibrate to emit the ultrasonic wave after time t1, at which the output of the oscillation pulse is stopped, the intensity of the ultrasonic wave, i.e., the voltage level of the piezoelectric element, is gradually attenuated. However, as can be clearly seen from the comparison of FIG. 4 with FIG. 4B, the attenuated degree of the waveform during resonance is small, whereas the attenuated degree of the waveform during non-resonance is great. Therefore, by utilizing the difference in attenuated degree of the waveform, it is possible to find a resonance frequency according to the wall thickness and material of the LPG tank 3.

For example, comparing the last waveform with the current waveform, assuming that the voltage level of the current waveform is higher than that of the last waveform at time t2 (or time t3 or t4), it can be seen at least that the frequency of the current waveform is closer to the resonance frequency. Therefore, by emitting the ultrasonic wave 6a predetermined times while varying the frequency and by selecting a waveform having the highest voltage level at time t2 therefrom, the selected waveform can be identified as the waveform at the resonance frequency, and this frequency can be determined as the operating frequency (step ST28). Alternatively, a predetermined threshold for the voltage level may be set, and a period of time until the voltage level is decreased to the threshold after the emission of the ultrasonic wave is started may be measured every waveform, so that a waveform having the longest time may be identified as the waveform at the resonance frequency.

After the operating frequency is determined as described above, the operating frequency setting means 9 writes the value of the determined operating frequency in the memory part 17 to register the written value (step ST29). Thereafter, the detection operation control circuit 8 outputs an ultrasonic wave emitting command to the variable oscillator circuit 11 so that an ultrasonic wave having the registered operating frequency is emitted from the detector 2. In addition, a field operator can simply operate the operating button 19 so that the operating frequency, which has been stored in the memory part 17, is displayed on the display part 18. Furthermore, while only the reflected waveform is detected at step ST25 in the above described example, both of the reflected waveform and the emission waveform may be detected to more precisely set the operating frequency.

By the way, the emission waveform comprises the pulse emitting waveform and the attenuation waveform as shown in FIGS. 4A and 4B, and the analysis at the above described step ST27 is carried out for finding the resonance frequency on the basis of the attenuated degree of the attenuation waveform of both waveforms. However, according to the present invention, the pulse emitting waveform may be utilized to find the resonance frequency on the basis of the value of impedance including the piezoelectric element of the detector 2 and the LPG tank 3.

Figure 5:
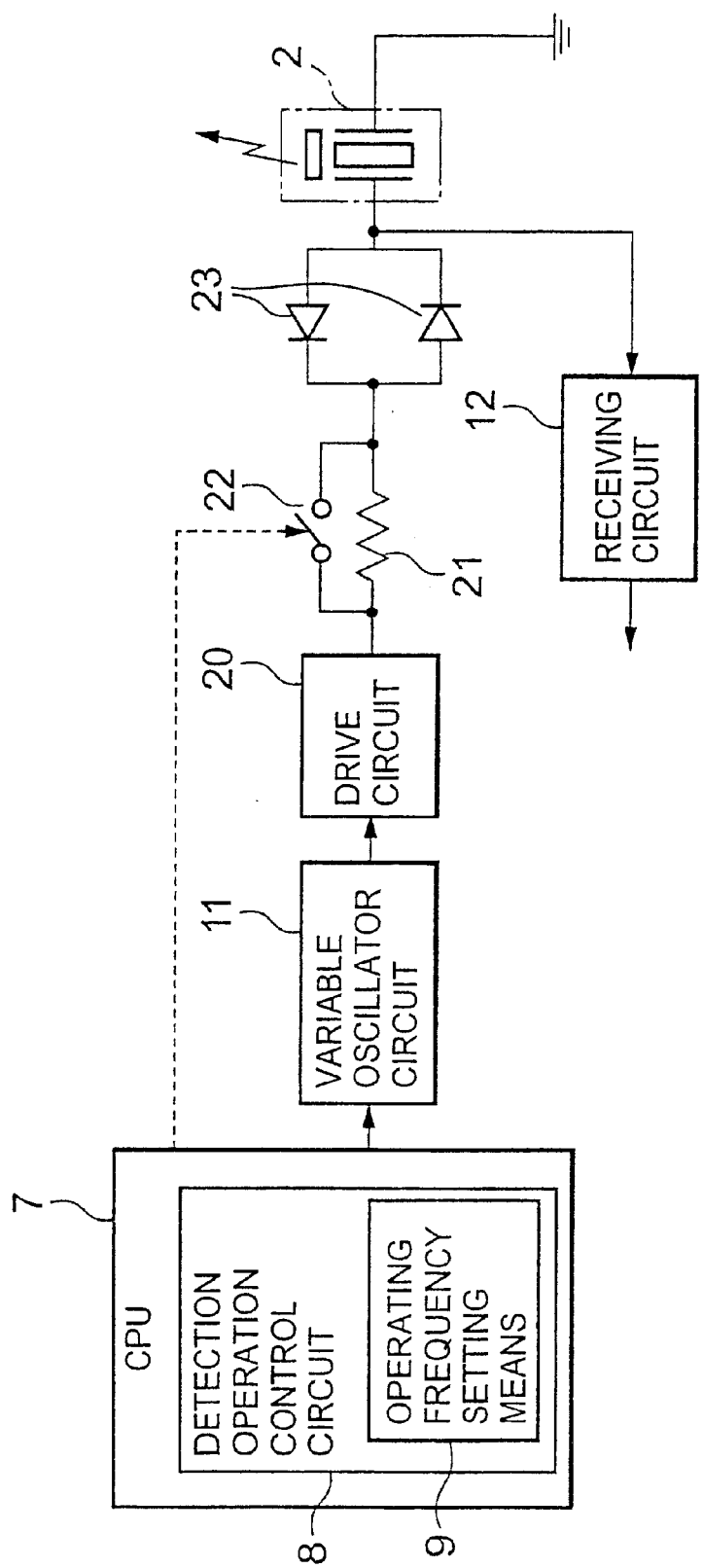
FIG. 5 is a diagram for explaining a principal part of the second preferred embodiment of the present invention.

FIG. 5 is a diagram for explaining a principal part of another preferred embodiment capable of finding the resonance frequency on the basis of the value of impedance. In this figure, a signal from the CPU 7 including the detection operation control circuit 8 having the operating frequency setting means 9 is outputted to the variable oscillator circuit 11. An oscillation pulse from the variable oscillator circuit 11 is outputted to the piezoelectric element of the detector 2 via a drive circuit 20, a resister 21, to which a switch 22 is connected in parallel, and a pair of diodes 23 inversely connected in parallel. At this time, the pulse emitting waveform and the attenuation waveform are received by the receiving circuit 12. The on-off control action of the switch 22 is controlled by the detection operation control circuit 8. Furthermore, in the second preferred embodiment shown in FIG. 5, only the resistor 21 and the switch 22 are newly added, and the drive circuit 20 and the pair of diodes 23 are omitted from FIG. 1.

The resistor 21 in FIG. 5 is provided so as to be capable of measuring the variation in voltage between both ends of the piezoelectric element of the detector 2. That is, when the drive circuit 20 applies a voltage between both ends of the piezoelectric element to emit an ultrasonic wave at the resonance frequency, the total impedance of the piezoelectric element and the LPG tank 3 is minimum, so that the current passing through the piezoelectric element is maximum. However, if the internal resistance of the drive circuit or drive power supply is sufficiently lower than the minimum impedance, even if the drive circuit 20 applies the voltage at the resonance frequency, the voltage between both ends of the piezoelectric element hardly varies, so that it is difficult to detect the variation thereof. Therefore, in this second preferred embodiment, as shown in FIG. 5, the resistor 22 is provided, and when the operating frequency is set, the detection operation control circuit 8 turns the switch 22 off to increase the load on the drive circuit 20 so that the variation in voltage between both ends of the piezoelectric element can be measured. In this case, the waveform used for the analysis at step ST27 by the operating frequency setting means 8 is the pulse emitting waveform of the emission waveform of FIG. 4, so that the frequency at the lowest voltage level of the pulse emitting waveform can be identified as the resonance frequency.

As described above, according to the detecting system using the ultrasonic sensor of the present invention, the detector 2 is mounted on the outside bottom face of the LPG tank 3, and before the liquid level control operation in the tank is carried out, the detector 2 emits the ultrasonic wave into the LPG tank a plurality of times in the operating frequency setting mode to detect the resonance frequency of the system comprising the detector and the tank by utilizing the resonance characteristic of the emission waveform or reflected waveform at that time to set the resonance frequency as the operating frequency. Therefore, the detecting system of the present invention can cope with the LGP tank 3 even if the wall thickness and material of the LPG tank are any wall thickness and material. In addition, since the operating frequency is automatically set, the installation of the ultrasonic sensor does not require the presence of any sensor manufacturer's experts, and can be simply carried out by only the user.

Furthermore, while the vessel for mounting thereon the detector has been the LPG tank in the above described first and second preferred embodiments, the vessel should not be limited to the LPG tank, but it may be any one of various vessels for use in various fields including chemical fields. In addition, the wall thickness and material of the vessel should not be limited to the above described thickness and material. In particular, the material may be selected from resin materials, such as plastics, in addition to metals.

Moreover, according to the present invention, while it has been an essential requirement to emit the ultrasonic wave from the detector a plurality of times while varying the frequency, it should not be swayed by wording and should be substantially interpreted whether the emission of the ultrasonic wave is carried out "a plurality of times". That is, when the ultrasonic wave is continuously emitted while varying the frequency, although it is estimated that there are different interpretations in accordance with the standpoint, such continuous emission should be a plurality of emissions, which should be included in the technical matters of the present invention.

Some devices for the technique for setting the operating frequency in the above described preferred embodiments will be described below.

(a) The oscillation pulse outputted from the variable oscillator circuit 11 to the piezoelectric element of the detector 2 is a rectangular wave pulse, not a sine wave pulse. This rectangular wave pulse includes all frequency components as can be seen from a mathematics formula for Fourier series. Therefore, even if the wall thickness and material of the vessel are widely changed, it is possible to sufficiently cope with such thickness and material. Furthermore, as can be clearly seen from the above described formula (1) or (2), in order to sufficiently cope with the wide changes in wall thickness and material of the vessel, the oscillation frequency is preferably as higher as possible.

(b) As shown in FIG. 1, in the first and second preferred embodiments, the band pass filter 14 is provided between the amplifier circuit 13 and the detector circuit 15, and the operating frequency setting means 9 analyzes waveform data transmitted via the band pass filter 14 to find a resonance point. Therefore, it is possible to prevent the false detection of the resonance frequency due to a higher harmonic oscillation. That is, as described in (a), since the output pulse of the variable oscillator circuit 11 is a rectangular wave pulse including all frequency components, there are some cases where there are apparently some resonance points other than the original resonance point in accordance with the high harmonic. However, since the band pass filter 14 is provided in this preferred embodiment, the frequencies other than the original resonance point are removed, so that it is possible to avoid the false detection of the resonance frequency due to the high harmonic oscillation. Furthermore, if the variable range of frequency is limited to a predetermined range, it is possible to omit the band pass filter 14. Conversely, when the band pass filter 14 is provided as this preferred embodiment, it is not required that the variable range of frequency should be limited to the predetermined range.

(c) As described in (b), the operating frequency setting means 9 inputs and analyzes waveform data transmitted via the band pass filter 14. In this case, of course, the waveform data are inputted via an A/D converter. If the conversion speed of the A/D converter is sufficiently high, there is no problem. However, if the conversion speed is low, there are some cases where it is not possible to follow the plurality of ultrasonic emitting timings, so that it is not possible to perform the A/D conversion of all waveform data. Such situation can be avoided by delaying each input timing of the waveform data from the band pass filter 14 to the operating frequency setting means 9 by a predetermined period of time. Thus, even if the conversion speed is low and an inexpensive A/D converter is used, it is possible to obtain the same effects as those when an A/D converter having a high conversion speed is used.

(d) In the first and second preferred embodiments, the piezoelectric element is formed of a low Q material. Therefore, if the oscillation frequency is varied when the operating frequency is set, the voltage level does not rapidly fluctuates, so that it is possible to easily detect the resonance point.

(e) In the first and second preferred embodiments, when the LPG tank 3 does not contain the liquid 4 therein, the waveform data are analyzed using the emission waveform, and when the LPG tank 3 contains the liquid 4 therein, the waveform data are analyzed using the reflected waveform. Therefore, it is possible to set the operating frequency regardless the gas injecting state in the LPG gas 3.

(f) In the first and second preferred embodiments, since the abnormality of the operating frequency is always monitored even during the usual operation after setting the operating frequency, it is possible to effectively cope with the variation in environment around the ultrasonic sensor. For example, when the mounting of the detector 2 is slacked by the vibration or impact applied to the LPG tank 3 due to some causes or by aged deterioration or the like, the set operating frequency is no longer the resonance frequency. In such a case, the operating frequency is automatically reset, or the operation itself is stopped. Then, the field operator can operate the operation button 19 on the basis of its determination, and reset the operating frequency in the operating frequency setting mode at any time.

Referring to FIGS. 6 through 14, the third through seventh preferred embodiments of the present invention with respect to the mounting of a detector 2 on a LPG tank 3 serving as a pressure vessel will be described below.

Figure 6:
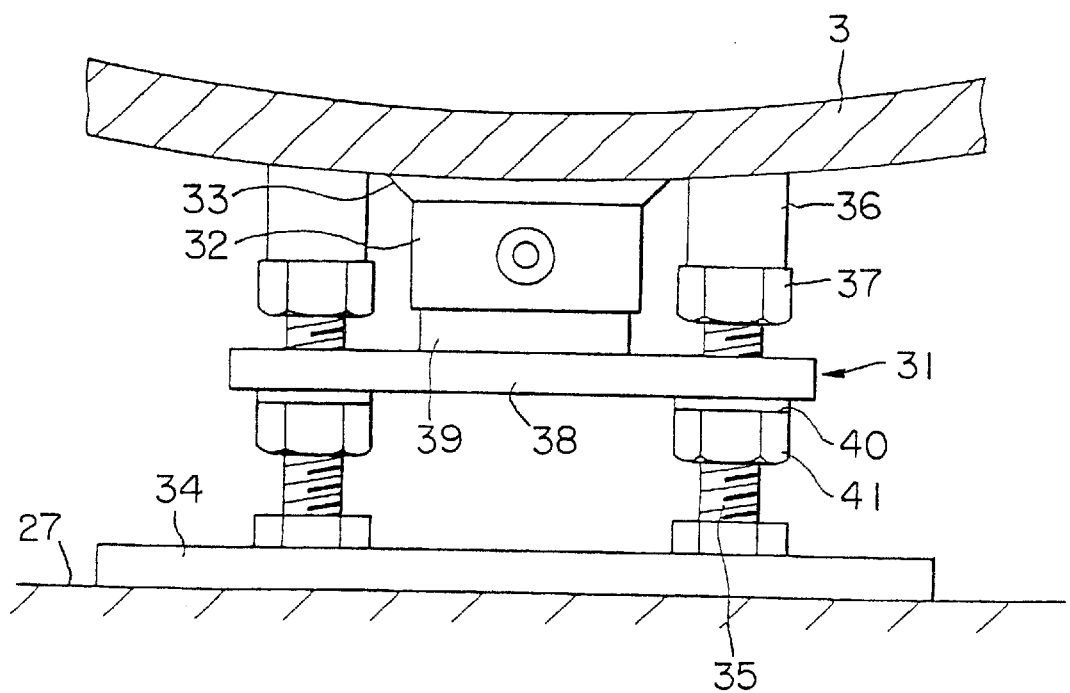
FIG. 6 is a sectional view of a structure for mounting a detector on a tank in the third preferred embodiment of an object detecting system according to the present invention.

In FIG. 6 showing the third preferred embodiment, detector case pressing means 31 is provided between the outside bottom face of a tank 3 and a floor face 27. The detector case pressing means 31 comprises: a fixed seat 34 mounted on the floor face 27; a plurality of hexagonal bolts (screw members) 35, the heads of which are welded to the top surface of the fixed seat 34; positioning sleeves 36, first nuts 37, washers 40, second nuts 41, which are mounted on the hexagonal bolts 35; and a movable plate 38, to which a mounting seat 39 is secured. On the mounting seat 39, a detector case 32 integrally formed with a packing 33 is mounted. The packing 33 tightly contacts the outside bottom face of the tank 3 having a curved shape.

Figure 7:
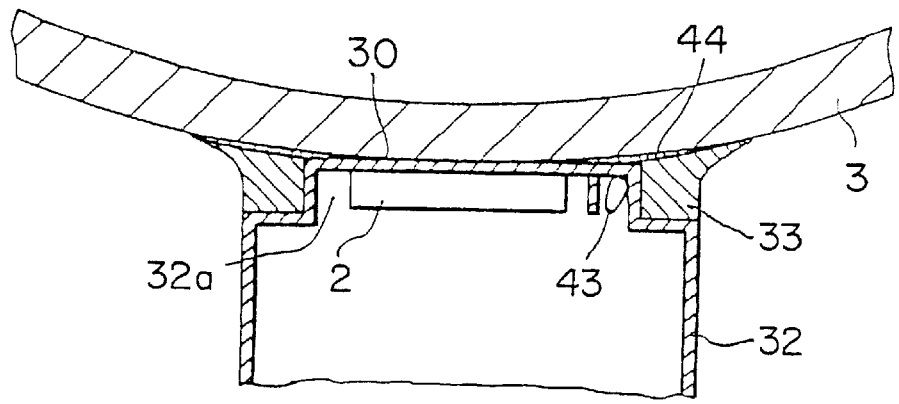
FIG. 7 is a sectional view showing the state that a detector case is mounted on the tank of FIG. 6.

In FIG. 7 which is a cross section showing the mounting state of the detector case 32 on the tank 3 of FIG. 6, a detector arranging space 32a is provided in an upper portion in the detector case 32, and the detector 2 and a thermocouple 43 are provided in the detector arranging space 32a. In addition, outside of the detector arranging space 32a, the packing 33 is integrally formed. Moreover, between the tank 3 and the detector case 32, a filler 44 having the same ultrasonic transmitting characteristic as that of the liquid 4 is provided. The filler 44 is uniformly and closely distributed on contact surfaces 30 on both sides.

Figure 8A:
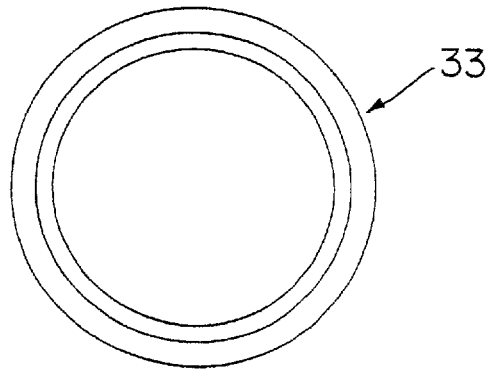
FIG. 8A is a plan view of a packing of FIG. 7.
Figure 8B:
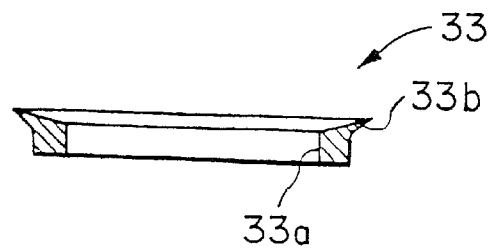
FIG. 8B is a longitudinal section of the packing of FIG. 7.

As shown in FIGS. 8A and 8B which are plan view and longitudinal section showing the shape of the packing 33, the packing 33 has a substantially ring shape, and comprises a cylindrical top portion 33a and a skirt portion 33b formed on one end of the cylindrical top portion 33a. The packing 33 is made of a soft resin, such as an elastomer, and can be easily deformed in accordance with the shape of the outside bottom face of the tank 3 having the curved surface. In addition, in the third preferred embodiment, the detector case 32 is made of a polyurethane, and the packing 33 is bonded to the detector case 32 after being produced as an independent member as shown in FIGS. 8A and 8B. However, the detector case 32 and the packing 33 may be integrally formed with each other by molding (double molding).

In FIGS. 9A, 9B and 9C which are plan, front and side views showing the detector case pressing means 31, a fixed seat 34 is a substantially rectangular thin plate member, two hexagonal bolts 35 are provided thereon so as to extend vertically, and the heads thereof are welded. On the screw portions of the hexagonal bolts 35, positioning sleeves 36, first nuts 37, a movable plate 38 of a substantially rectangular thin plate member, washers 40 and second nuts 41 are mounted in that order from the top. To the central portion of the movable plate 38, a mounting seat 39 for mounting thereon a detector case 32 of a substantially square thin plate member is secured. The positioning sleeve 36 is formed of a rubber member so that the upper end portion thereof can be easily deformed when it contacts the outside bottom face of the tank 3 having a curved shape.

Figure 10:
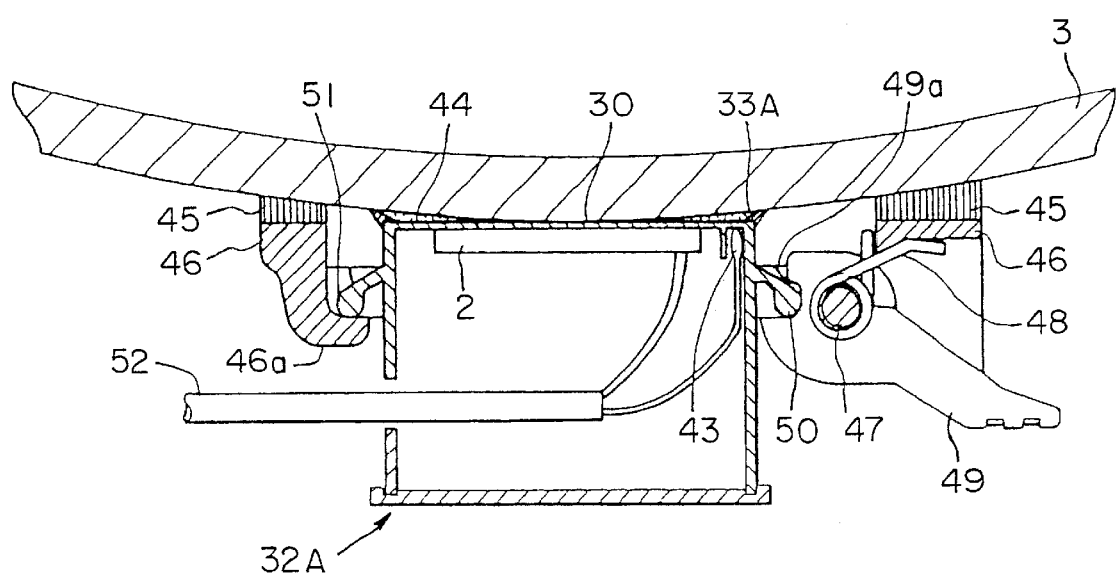
FIG. 10 is a sectional view of a structure for mounting a detector case on a newly produced vessel in the fourth preferred embodiment of a detecting system according to the present invention.

FIG. 10 shows the fourth preferred embodiment of the present invention. The third preferred embodiment is effective in the mounting of the detector case on the prepared tank 3, whereas the fourth preferred embodiment is effective in the mounting of a detector case on a newly produced vessel. In FIG. 10, a mounting base 46 is secured to the outside bottom face of a tank 3 via a spacer 45 at a predetermined position. The spacer 45 and the mounting base 46 are made of a polyurethane. In the factory, the spacer 45 is previously secured to the outside bottom face of the tank 3 at a predetermined position by an adhesive, and the mounting base 46 is secured to the spacer 45 by an adhesive. The reason why this preferred embodiment is more suitable for the newly produced tank than the prepared tank 3 is that it is difficult to precisely identify the predetermined position, at which the spacer 45 is to be secured, in a narrow operation space.

On the mounting base 46, a mounting lever 49 having a pin 47 and a coil spring 48 is mounted. The mounting lever 49 has a recessed portion 49a which engages an engaging protrusion 50 formed in a detector case 32A (of a polyurethane). The detector case 32A also has an engaging protrusion 51 on the opposite side to the engaging protrusion 50. The engaging protrusion 51 engages an engaging portion 46a of the mounting base 46. Furthermore, one end of a cable 52 is introduced into the detector case 32A, and a detector 2 and a thermocouple 43 are connected to a body 1 (see FIG. 1) via the cable 52.

On the upper end surface of the detector case 32A, a packing 33A of an elastomer is integrally formed by a double molding. On the contact surface 30, a filler 44 is uniformly and closely provided. Furthermore, in this preferred embodiment, detector case pressing means comprises the mounting base 46, the mounting lever 49, the coil spring 48 and the engaging protrusions 50, 51 of the detector case 32A.

As shown in FIGS. 11A, 11B and 11C which are plan, sectional and bottom views showing the shape of the mounting base 46 of FIG. 10, the mounting base 46 substantially has the shape of a horseshoe. One end of the mounting base 46 has an engaging portion 46a engaging an engaging protrusion 51 of a detector case 32A, and the other end thereof has a hole 46b for allowing a pin 47 to pass therethrough. In addition, reference number 46c denotes a flat mounting face for a spacer 45, and reference number 46d denotes an opening having a greater diameter than the outer diameter of the detector case 32A.

Figure 12:
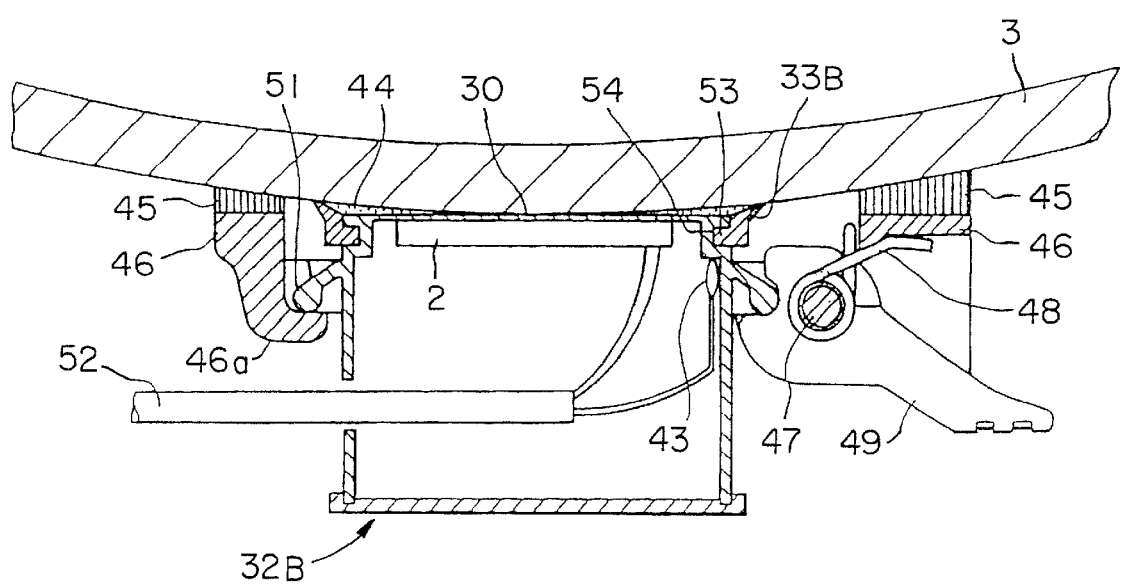
FIG. 12 is a sectional view of a structure for mounting a detector case on a newly produced vessel in the fifth preferred embodiment of a detecting system according to the present invention.

The fifth preferred embodiment is substantially the same as the fourth preferred embodiment, except that a packing is secured to a detector case after it is produced as a separate member from the detector case. In FIG. 12 showing the fifth preferred embodiment, an annular groove portion 54 is formed in the top of a detector case 32B, and an annular projecting portion 53 is formed on a packing 33B. Both are surely secured to each other by an adhesive while the projecting portion 53 engages the groove 54. With this construction, the detector case 32B and the packing 33B of different materials can be easily produced as separate members at the beginning, and thereafter, the engaging portions of both members have only to be secured to each other. Therefore, the packing 33B can be integrally formed with the detector case 32B without the need of the double molding. In this preferred embodiment, other constructions are the same as those of the fourth preferred embodiment, so that the description thereof is omitted.

Figure 13:
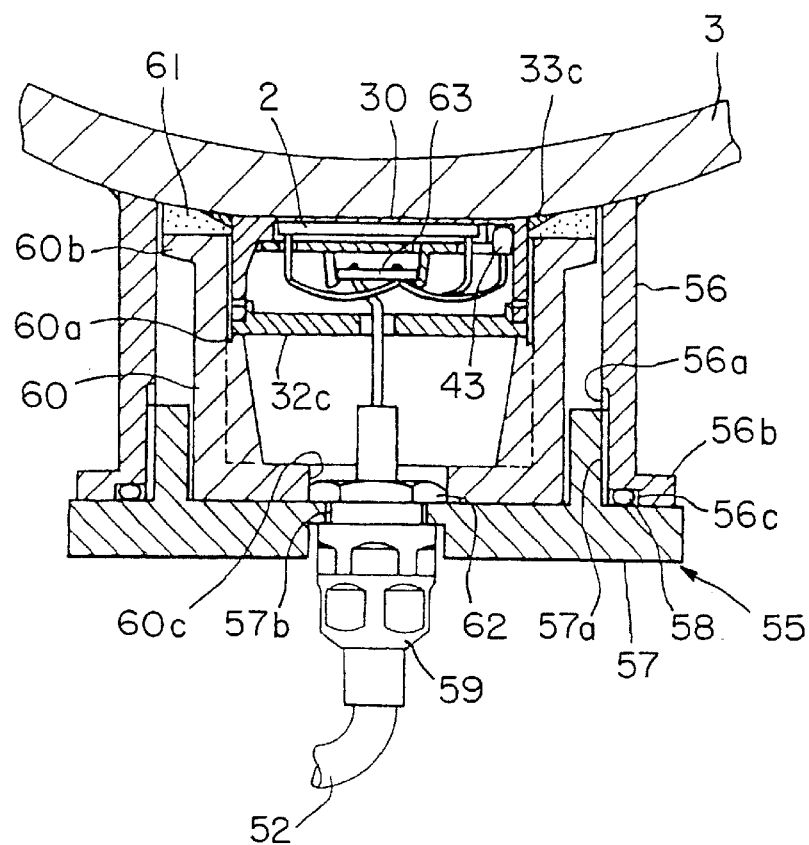
FIG. 13 is a sectional view of a structure for mounting a detector case on a tank by a waterproof construction in the sixth preferred embodiment of a detecting system according to the present invention.

FIG. 13 shows the sixth preferred embodiment of the present invention wherein a waterproof construction is utilized to press a detector case 32 against the outside bottom face of a tank 3. Similar to the fourth and fifth preferred embodiments, the sixth preferred embodiment is also effective in the mounting of a detector case on a newly produced vessel. In FIG. 13, a waterproof cover 55 comprises a cylindrical body 56 and a lid 57. The upper end portion of the cylindrical body 56 is welded to the outside bottom face of a tank 3, and a screw portion 56a is formed in the inner peripheral surface of the lower end portion of the cylindrical body 56. On the other hand, a screw portion 57a is also formed in the lid 57. The lid 57 is engaged with the cylindrical body 56 by means of the screw portions 56a and 57a. The cylindrical body 56 has a flange portion 56a. An O-ring 58 is provided in an annular groove 56c formed in the flange portion 56a to accomplish the waterproof function of the waterproof cover 55.

In the waterproof cover 55, a pressing block 60 serving as detector case pressing means is provided. In the pressing block 60, a detector case 32C integrally formed with a skirt-shaped packing 33C is provided. In the pressing block 60, a stepped portion 60a is formed. The stepped portion 60a presses the detector case 32C against the outside bottom face of the tank 3. In addition, a stop portion 60b is formed on the upper end portion of the pressing block 60, and a sponge packing 61 is secured to the stop portion 60b. The sponge packing 61 presses the packing 33C against the outside bottom face of the tank 3.

A threaded hole 57b is formed in the central portion of the lid 57, and engages a connector 59 mounted on the end of the cable 52. In addition, a nut 62 is mounted on the upper portion of the screw portion of the connector 59 which is fixed to the lid 57 by means of the nut 62. Moreover, a hole 60c is formed in the pressing block 60, and houses therein the nut 62. The hole 60c has the shape of a hexagonal corresponding to the nut 62 so as to restraint the relative rotation between the pressing block 60 and the nut 62. A lead wire is introduced into the detector case 32C from the end of the cable 52 extending above the nut 62. This lead wire is connected to the detector 2 and the thermocouple 43 via a terminal block 63. Furthermore, a potting material is filled in the detector case 32C to surely carry out the fixing of the terminal block 63 and the wiring materials, such as the lead wire.

As described above, according to the sixth preferred embodiment, when the detector case and the packing are fixed to the vessel installed out of doors, it is possible to realize the waterproof construction. In addition, by utilizing the waterproof construction, it is possible to simply carry out the fixing operation, and it is possible to uniformly and closely distribute the filler between the close contact faces of the detector case and the outside bottom face of the vessel.

Figure 14:
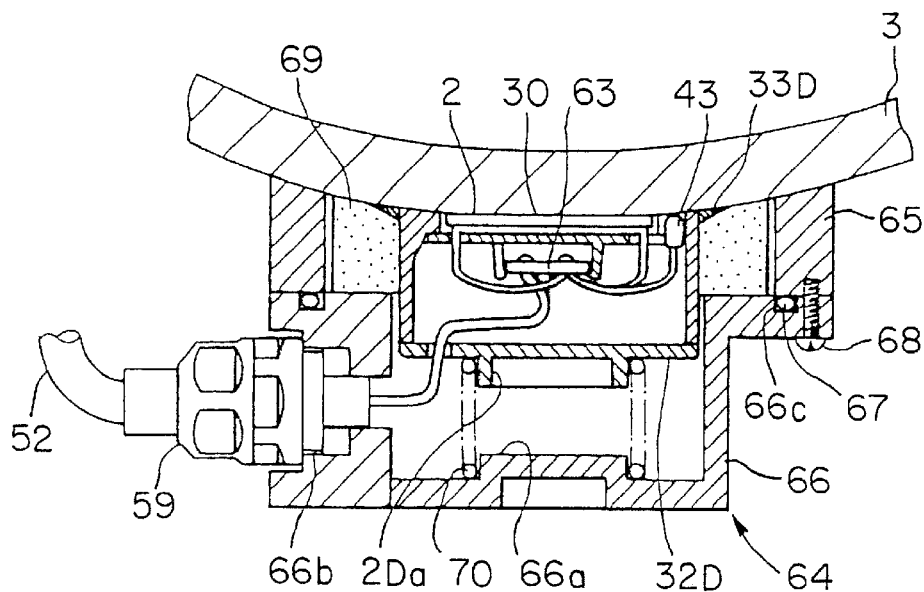
FIG. 14 is a sectional view of a structure for mounting a detector case on a tank by a waterproof construction in the seventh preferred embodiment of a detecting system according to the present invention.

FIG. 14 shows the seventh preferred embodiment of the present invention. Similar to the sixth preferred embodiment, the seventh preferred embodiment also uses a waterproof construction. In the seventh preferred embodiment, a coil spring is used as detector case pressing means. In addition, in the seventh preferred embodiment, a detector closely contacts the outside bottom face of a vessel.

In FIG. 14, a waterproof cover 64 comprises a cylindrical body 65 and a lid 66. The upper end portion of the cylindrical body 65 is welded to the outside bottom face of a tank 3, and the lid 66 is mounted on the lower end portion thereof by means of a mounting screw 68. An annular groove 66c is formed in the inside face of the flange portion of the lid 66 facing the cylindrical body 65, and an O-ring 67 is mounted in the annular groove 66c to realize a waterproof construction.

A sponge packing 69 is provided in the cylindrical body 65, and a detector case 32D integrally formed with a skirt-shaped packing 33D is provided in the sponge packing 69. The upper portion of the detector case 32D is open so that the upper end face 2a of a detector 2 closely contacts the outside bottom face of the tank 3. A circular mounting seat 2Da is formed on the bottom face of the detector case 32D, and a mounting seat 66a is also formed on the inside face of the lid 66 so as to face the mounting seat 2Da. A coil spring 70 is mounted on the mounting seats 2Da and 66a to bias the detector case 32D toward the tank 3.

In addition, a threaded hole 66b is formed on the side portion of the lid 66, and a connector 59 mounted on the end of a cable 52 engages the threaded hole 66b. A lead wire extending from the connector 59 is introduced into the detector case 32D. The lead wire is connected to the detector 2 and a thermocouple 43 via a terminal block 63. In the sixth preferred embodiment, the connector 59 has been mounted on the bottom face of the waterproof cover 55, whereas in the seventh preferred embodiment, the connector 59 is mounted on the side of the waterproof cover 64, so that it is possible to easily carry out a mounting operation even if the space between the outside bottom face of the tank 3 and a floor face 27 is narrower.

As described above, according to the seventh preferred embodiment similar to the sixth preferred embodiment, it is possible to utilize the waterproof construction to simply carry out the fixing operation of the detector case and to uniformly and closely distribute a filler between the close contact faces of the detector and the outside bottom face of the vessel. In addition, since the seventh preferred embodiment uses the coil spring as detector case pressing means, the height of the waterproof cover in the seventh preferred embodiment can be smaller than that in the sixth preferred embodiment, and the seventh preferred embodiment is suitable for operation in a narrow space.

Furthermore, in the above described third through seventh preferred embodiments, only a grease-like filler has been injected onto the upper end face of the detector case or detector, and the upper end face of the detector case or detector has been pressed against the outside bottom face of the vessel. However, it has been confirmed from the results of the inventor's experiment that the distributed state of the filler can be better to improve the precise of the ultrasonic sensor if the detector is fixed so that the upper end face of the detector faces the outside face of the detector case, to inject a filler (a fixing filler) containing an epoxy resin or the like as a main component onto the upper end face of the detector to solidify the filler to sufficiently polish the surface of the fixing filler to inject the grease-like filler. Therefore, such a fixing filler can be suitably used in accordance with the actually required precision.

As described above, according to the third through seventh preferred embodiments of the present invention, the detector case is integrally formed with the skirt-shaped packing member of a soft resin for holding the filler between the close contact faces of the detector case and the outside bottom face of the vessel, and the detector case is pressed against the outside bottom face of the vessel by the detector case pressing means. Therefore, the filler can be uniformly and closely distributed between the close contact faces, and the detector case can be easily mounted on the outside bottom face of the vessel even in a narrow space.

What is claimed is:

1. An object detecting system using an ultrasonic sensor, said object detecting system comprising:

a detector for being mounted on an outside face of a vessel;

operating frequency setting means for causing said detector to emit an ultrasonic wave a plurality of times while varying a frequency, for inputting an emission waveform or a reflected waveform at that time, for detecting a resonance frequency of a system comprising said detector and said outside face of said vessel on the basis of an analysis of the inputted waveform, and for setting the detected resonance frequency as an operating frequency; and a detection operation control circuit for causing said detector to emit the ultrasonic wave toward an object to be detected in said vessel and to receive a reflected wave from said object, and for controlling an object detecting operation on the basis of a measured period of time between the ultrasonic wave emitting time and the reflected wave receiving time.

2. An object detecting system as set forth in claim 1, wherein said detector emits said ultrasonic wave in response to the input of a rectangular pulse signal.

3. An object detecting system as set forth in claim 2, wherein said operating frequency setting means inputs said emission waveform or said reflected waveform used for said analysis, via a band pass filter to prevent a false detection of said resonance frequency due to a high harmonic oscillation.

4. An object detecting system as set forth in claim 1, wherein said vessel is used for storing therein a liquid, and said operating frequency setting means determines whether said analysis is carried out using said emission waveform or said reflected waveform, on the basis of the presence of said liquid in said vessel.

5. An object detecting system as set forth in claim 1, wherein said analysis of said emission waveform or said reflected waveform carried out by said operating frequency setting means includes the selection of a waveform having a minimum attenuated degree of an attenuation waveform from said emission waveform and said reflected waveform, and the derivation of an operating frequency of the selected waveform.

6. An object detecting system as set forth in claim 1, wherein said analysis of said emission waveform or reflected waveform carried out by said operating frequency setting means includes the selection of a waveform having the minimum impedance including said detector and said vessel, and the derivation of an operating frequency of the selected waveform.

7. An object detecting system as set forth in claim 1, wherein said operating frequency setting means shifts each input timing from the last input timing by a predetermined period of time when a plurality of emission waveforms or reflected waveforms are inputted on the basis of the plurality of emissions of said ultrasonic wave.

8. An object detecting system as set forth in claim 1, wherein said detector has a piezoelectric element formed of a low Q material having a gentle resonance waveform (Q) so that an acutance of the resonance waveform decreases.

9. An object detecting system as set forth in claim 1, wherein said detector has temperature detecting means for detecting the temperature of the outside face of said vessel, and supplies a temperature compensation based on the temperature detected by said temperature detecting means, to said operating frequency setting means.

10. An object detecting system as set forth in claim 1, wherein said detector comprises a case and said object detecting system further comprises:

a cylindrical body, having one end welded to a bottom of said outside face of said vessel;

a lid mounted on another end of said cylindrical body by means of a screw member;

a waterproof cover housing therein said detector case; and a detector case pressing means comprising a coil spring, mounted on an inside face of said lid, for applying a pressing force toward said bottom of said outside face of said vessel to said detector case.

11. An object detecting method using an ultrasonic sensor having a detector on an outside face of a vessel for causing said detector to emit an ultrasonic wave toward an object to be detected in said vessel and to receive a reflected wave from said object and for detecting said object on the basis of a measured period of time between the ultrasonic wave emitting time and the reflected wave receiving time, said object detecting method comprising the steps of:

causing said detector to emit an ultrasonic wave a plurality of times while varying: a frequency before said object is detected;

inputting an emission waveform or a reflected waveform at that time;

detecting a resonance frequency between a system comprising said detector and said outside face of said vessel on the basis of an analysis of the inputted emission waveform or reflected waveform;

setting the detected resonance frequency as an operating frequency; and causing said detector to emit an ultrasonic wave toward said object to be detected in said vessel, on the basis of the set operating frequency.

12. An object detecting method as set forth in claim 11, which further comprises the steps of:

detecting the temperature of said outside face of said vessel;

calculating a temperature compensation amount on the basis of the detected temperature of said outside face of said vessel; and correcting said operating frequency on the basis of the calculated temperature compensation amount.

* * * * *